United States Patent

Yamaguchi et al.

Patent Number: 5,051,494
Date of Patent: Sep. 24, 1991

[54] THERMOSETTING RESIN COMPOSITION COMPRISING AN AROMATIC AMINE

[75] Inventors: Keizaburo Yamaguchi, Kawasaki; Yoshimitsu Tanabe; Tatshuiro Urakami, both of Yokohama; Akihiro Yamaguchi, Kamakura; Norimasa Yamaya; Masahiro Ohta, both of Yokohama, all of Japan

[73] Assignee: Mitsui Toatsu Chemicals, Inc., Tokyo, Japan

[21] Appl. No.: 511,235

[22] Filed: Apr. 19, 1990

Related U.S. Application Data

[62] Division of Ser. No. 254,701, Oct. 7, 1988, Pat. No. 4,937,318.

[30] Foreign Application Priority Data

Oct. 8, 1987 [JP] Japan .................................. 62-252517
Nov. 10, 1987 [JP] Japan .................................. 62-282048
Dec. 9, 1987 [JP] Japan .................................. 62-309426

[51] Int. Cl.$^5$ ...................... C08G 73/10; C08L 33/24
[52] U.S. Cl. ................................... 528/422; 528/397; 528/425
[58] Field of Search ................ 528/422, 322, 397, 425

[56] References Cited

OTHER PUBLICATIONS

Journal of Polymer Science, vol. 8, 1970 "Phosphorus-Containing Polyurethanes" E. Dyer et al.
Chemical Abstracts, vol. 108, 1988 "Epoxy Containing Condensed Polycyclic Aromatic Resins" Tsuyukuch et al.

Primary Examiner—John Kight, III
Assistant Examiner—T. Mosley
Attorney, Agent, or Firm—Burns, Doane, Swecker & Mathis

[57] ABSTRACT

The invention relates to an aromatic amine resin comprising a mixture of aromatic amine compounds represented by the following general formula (a):

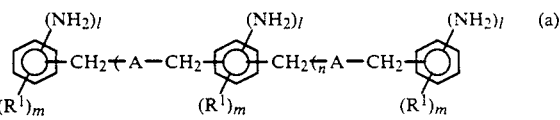

wherein A represents a phenylene, alkyl-substituted phenylene, diphenylene, diphenyl ether or naphthylenyl group, $R^1$ represents a halogen atom or a hydroxyl $C_{1-4}$ alkoxy or $C_{1-5}$ alkyl group, l is 1 or 2, m is 0, 1, 2 or 3, n is an integer from 0 to 300 and when m is 2 or 3, the $R^1$ group may be the same or different and may join to form a 5- or 6-membered alicyclic moiety which may optionally contain one or more side chains, and also relates to processes for producing the same and a thermosetting composition containing the same.

7 Claims, 1 Drawing Sheet

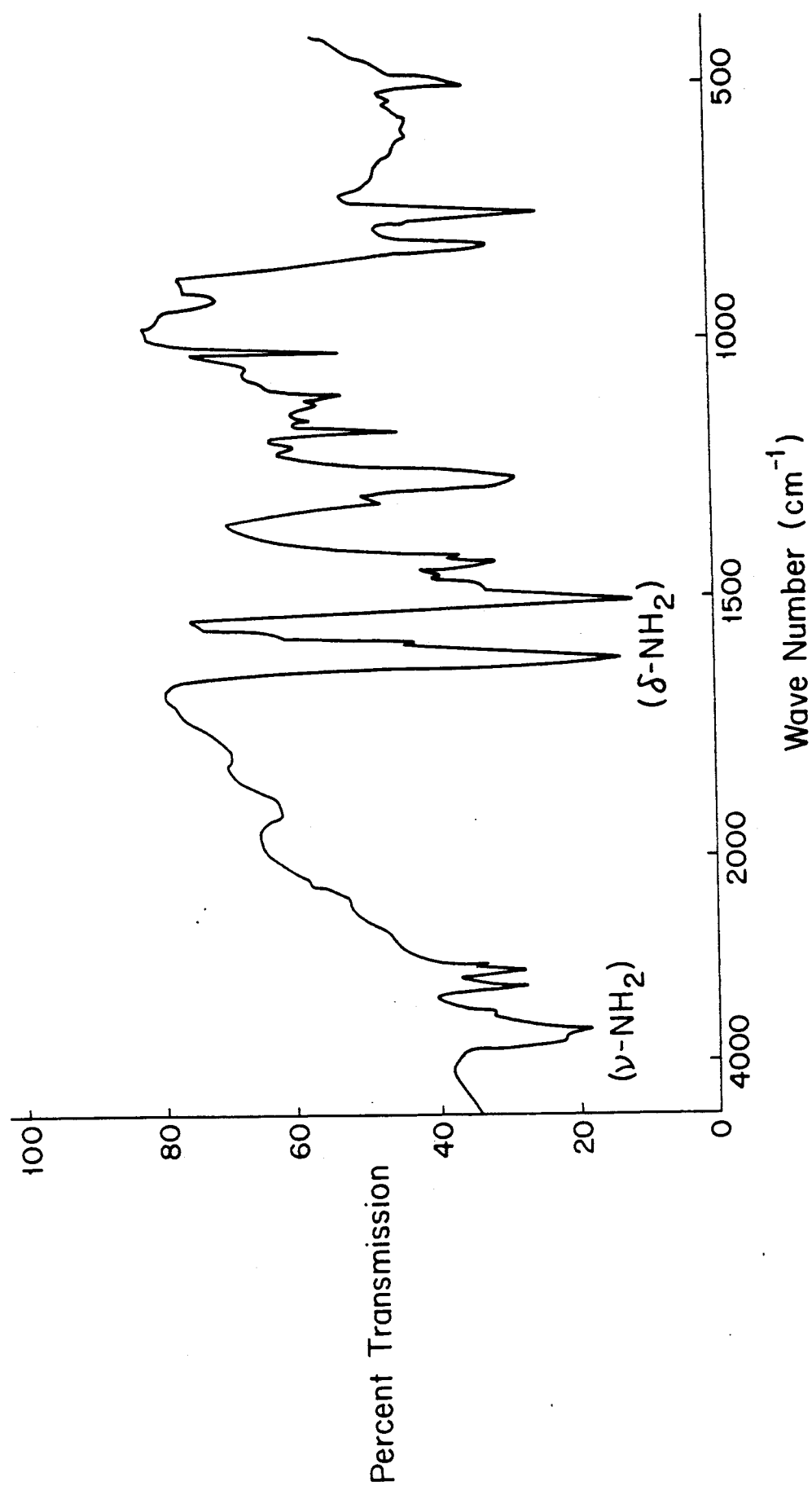

THERMOSETTING RESIN COMPOSITION COMPRISING AN AROMATIC AMINE

This application is a divisional of application Ser. No. 254,0701, filed Oct. 7, 1988 U.S. Pat. No. 4,937,318.

BACKGROUND OF THE INVENTION (1) Field of the Invention

This invention relates to novel aromatic amine resins, processes for producing the same and thermosetting resin compositions containing the aromatic amine resins.

(2) Description of the Related Art

It has been known for many years that aromatic amine resins are condensation products of aromatic amines and formaldehyde. For example, an aniline-formaldehyde resin represented by the following general formula (f):

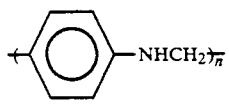

has been produced [K. Frey, Herbetica Chemie Acta, 18, 481 (1935)].

However, it is difficult to introduce maleimide or isocyanate groups into conventional aromatic amine resins such as an aniline-formaldehyde resin represented by the general formula (f). Such amine resins are hence not suitable as raw materials for maleimide resins or isocyanate resins. Conventional aromatic amine resins have therefore been used widely as curing agents. Today, increasingly sophisticated application and more rigorous expectation in performance and consistency of performance require that aromatic amine resins be suitable for use in matrix resins of heatresistant composite materials, high-temperatureresistant bonding agents and the like. These demands can no longer always be met adequately by conventional aromatic amine resins.

Heat-resistant composite materials, high-temperature-resistant bonding agents, and the like are required to withstand instantaneous impact such as stress concentration from an external stress. Ideally, the ability of undergoing an elastic deformation like rubber is an important and highly desirable property. The elastic deformation property of a resin is evaluated by measuring the elongation at a break of each matrix resin. The greater the elongation of the matrix resin, the greater the overall strength of a composite material. Thus, the drawbacks of the presence of a reinforcing material such as glass fibers or carbon fibers required for a composite material can be compensated.

For such matrix resins and the like, long-term storage stability, heat resistance and dimensional stability are also important properties. Such resins are also required to undergo less deterioration by light or oxygen in the air. This oxidation resistance is primarily attributable to the structure of each resin. In addition to failing to satisfy the abovementioned demands for mechanical strength, conventional aromatic amine resins involve difficulties in overcoming various drawbacks which are attributed to their structural defects.

The aniline-formaldehyde resin represented by formula (f) above; is converted into a crosslinked structure when the molar ratio of formaldehyde is increased upon condensation thus increasing the degree of condensation and improving its mechanical properties and the like. Accordingly, it is only possible to increase the molecular weight of such a resin to about 600 [Noda, et al., Nippon Kogyo Kagaku Zasshi, 55, 484–487 (1952)].

The present inventors have already discovered novel aromatic amine resins which have improved upon these drawbacks. A patent application covering such aromatic amine resins was filed on Sept. 17, 1987 in Japan (Japanese Patent Application No. 230987/1987). However, since these resins are composed of a secondary amine, it is difficult to achieve isocyanation or maleimidation. They are accompanied by further problems such that when used as a curing agent, these resins must be employed in a relatively large amount and their curing speeds are relatively slow.

On the other hand, thermosetting resins having an imide structure have already found wide-spread industrial utility due to their excellent electrical insulation, heat resistance and dimensional stability of moldings.

However, thermosetting resins which are obtained by separately subjecting aromatic bismaleimides to heat polymerization have drawbacks such as being extremely brittle and having poor flexibility. As a method for improving such drawbacks, it has been attempted to use a thermosetting resin composition composed of an aromatic bismaleimide and an aromatic diamine. For example, a polyaminobismaleimide resin ("Kerimid", trade mark; product of Rhone-Poulanc S.A.) composed of N,N'-4,4'-diphenylmethanebismaleimide and 4,4'-diaminodiphenylmethane has been used widely in impregnating varnishes, laminated boards, moldings, etc. (Japanese Patent Publication No. 23250/1971).

However, such thermosetting resin compositions do not have sufficient heat resistance and are not satisfactory either in impact resistance or flexibility.

SUMMARY OF THE INVENTION

A first object of this invention is to provide a novel aromatic amine resin which when used as a curing agent, provides a cured resin having excellent heat resistance, mechanical strength, dimensional stability, and light and air oxygen stability and which is also useful as a raw material for isocyanate resins, maleimide resins and the like.

A second object of this invention is to provide a novel process for the production of the above aromatic amine resin.

A third object of this invention is to provide a process that is more economical, less costly, and produces less side reactions than prior art processes.

A fourth object of this invention is to provide a novel thermosetting resin composition having excellent mechanical strength and heat resistance.

The present invention overcomes the problems and disadvantages of the prior art by providing an aromatic amine resin which when used as a curing agent provides a curing resin having superior properties. In one aspect of this invention, there is thus provided an aromatic amine resin formed of a mixture of aromatic amine compounds represented by the following general formula (a):

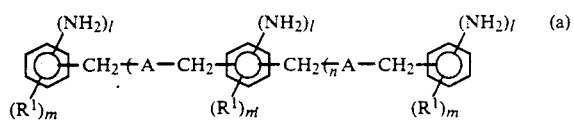

wherein A represents a phenylene, alkyl-substituted phenylene, diphenylene, diphenyl ether or naphthylenyl group; $R^1$ represents a halogen atom or a hydroxyl; $C_{1-4}$ alkoxy or $C_{1-5}$ alkyl group; l is 1 or 2; m is an integer from 0 to 3; when m is 2 or 3, $R^1$ may be the same or different and two of $R^1$ groups may join together to form a 5- to 6-membered alicyclic moiety which may contain one or more side chains; and n represents an integer of from 0–300.

In another aspect of this invention, there is also provided a first process for the production of the above aromatic amine resin, which comprises reacting in the presence of an acid catalyst an aromatic amine represented by the following general formula (b):

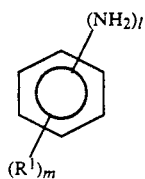
(b)

wherein $R^1$, l and m have the same meanings as defined with respect to formula (a), with an aralkyl alcohol derivative represented by the following general formula (c):

$$R^2OCH_2-A-CH_2OR^2 \qquad (c)$$

wherein A has the same meaning as defined with respect to formula (a) and $R^2$ is a hydrogen atom or an acyl or $C_{1-4}$ alkyl group.

In a further aspect of this invention, there is also provided a second process for the production of the above aromatic amine resin, which comprises reacting the aromatic amine of the formula (b) with a bishalogenomethyl derivative represented by the following general formula (d):

$$X-CH_2-A-CH_2-X \qquad (d)$$

wherein A has the same meaning as defined with respect to formula (a) and X is a halogen atom. The reaction of this process can be conducted even in the absence of any catalyst.

In a still further aspect of this invention, there is also provided a novel thermosetting resin
composition comprising 100 parts by weight of N,N'-4,4'-diphenylmethanebismaleimide represented by the following formula (e):

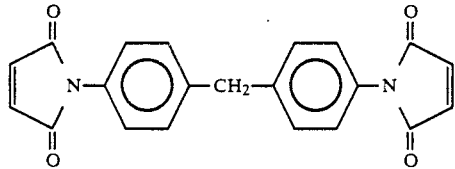
(e)

and 5–100 parts by weight of the aromatic amine resin represented by the general formula (a).

BRIEF DESCRIPTION OF THE DRAWING

FIG. 1 diagrammatically shows results of an IR analysis of an aromatic amine resin obtained in Example 1.

DETAILED DESCRIPTION OF THE INVENTION

The aromatic amine resins according to this invention can be used in a wide variety of fields, for example, as raw materials for epoxy resins or curing agents for other epoxy compounds, as raw materials for maleimide resins or curing agents for other maleimide compounds, as raw materials for isocyanate resins or curing agents for other isocyanate compounds, as chelate, resins, ion-exchange resins, molding materials, insulating paints, bonding agents, rubber modifiers, additives for various resins, deacidification agents, and as raw materials for polyimides, polyamides and polyamideimides, etc.

Since the aromatic amine resins according to this invention are composed of a primary amine, it is easy to achieve isocyanation, maleimidation or epoxidation.

Further, resins having high performance can be obtained by using the aromatic amine resins of this invention as curing agents for other resins (for example, isocyanate compounds, epoxy compounds, bismaleimide compounds, etc.).

When the resins according to this invention are used as curing agents for bismaleimide compounds, the resultant cured resins exhibit excellent mechanical strength, dimensional stability, heat resistance and light and air oxygen stability. Their curing speeds are also high. For example, use of any one of the resins according to this invention as a curing agent for bismaleimide derived from methylenedianiline can provide a cured resin whose flexural strength, flexural modulus, pyrolysis starting temperature in air, coefficient of expansion and water absorption rate are superior to those of "Kerimid 1050" (trade name; molding grade; product of Rhone-Poulanc S.A.) obtained by using methylene-dianiline as a curing agent. Their glass transition temperatures and heat distortion temperatures are substantially comparable.

In addition, the resins according to this invention are soluble in low boiling point solvents (dioxane, methylene chloride, etc.).

A prepreg has heretofore been prepared by dissolving a prepolymer such as "Kelimide" in a high boiling point aprotic polar solvent (N-methylpyrrolidone or the like) and then impregnating glass cloth or carbon cloth with the solution. In contrast to such a conventional method, use of any one of the resins according to this invention as a prepolymer facilitates the evaporation and removal of the solvent to provide an excellent prepreg since the resin can be dissolved in a low boiling point solvent.

The resins according to this invention are faster in curing speed than the resins disclosed previously by the present inventors in Japanese Patent Application No. 230987/1987. Thus, the former resins are preferred particularly for use as sealing resins for semiconductors.

The first production process according to the present invention will next be described.

The resins according to this invention can each be produced by subjecting the aromatic amine compound represented by the general formula (b) and the aralkyl alcohol derivative represented by the general formula (c) to a co-condensation reaction. If aniline and the aralkyl alcohol derivative are caused to undergo co-condensation in the course of the reaction, a resin containing a secondary amine such as that having a structure of the following formula (g):

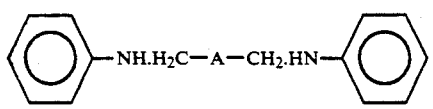

is formed. It is however only necessary to convert the secondary amine resin into a primary amine resin of this invention by a rearrangement reaction. This rearrangement reaction can be conducted, for example, by (a) increasing the amount of the catalyst, (b) by increasing the reaction temperature or (c) by increasing the reaction time compared to the reaction conditions under which the secondary amine is formed. In particular, it is effective to increase the amount of the catalyst.

As already mentioned above, it has been only possible to increase the molecular weight of the conventionally-known aniline-formaldehyde resin to about 600. In contrast, the aromatic amine resins according to this invention may each be chosen as desired from a low molecular resin composed principally of the aromatic amine compound of the general formula (a) in which n is 0, to a high molecular resin composed of the aromatic amine compound principally of the general formula (a) in which n is about 300. Thus, by the first production process of this invention, aromatic amine resins ranging in a form from a liquid resin at room temperature to a high softening point resin in a resinous form can be produced, depending upon the intended end use.

Resins according to this invention, ranging from liquid resins to those having a low softening point, can be obtained provided that the molar ratio of the aromatic amine compound to the aralkyl alcohol derivative is increased. The liquid-low softening point resins thus obtained are excellent in workability upon melt blending, impregnation, coating and the like and are useful as bonding agents, paints, and additives for urethane and other resins.

High softening point resins according to this invention can be obtained provided that the molar ratio of the aralkyl alcohol derivative to the aromatic amine is near a stoichiometric ratio upon their condensation. The high softening point resins obtained are useful as molding materials, ion-exchange resins and laminating resins.

The molecular weight range of the aromatic amine resins obtained as described above in accordance with the first production process of this invention range from about 300 to about 60,000. The softening point of the resins range from a liquid state at room temperature to about 250.C (as ring and ball softening points measured in accordance with JIS-K-2548).

In the first process of the invention, the aromatic amine compound represented by the general formula (b) is preferably employed in an amount of from about 1–15 moles, more preferably from about 1.1–10 moles per mole of the aralkyl alcohol derivative represented by the general formula (c). The compounds are heated in the presence of an acid catalyst. Water, alcohol, organic acid and/or the like, which are formed as the reaction proceeds, are trapped outside the system. Volatiles which remain at trace levels within the system may be purged out with nitrogen if necessary. When it is desired to obtain a relatively low molecular resin composed principally of the aromatic amine compound of the general formula (a) in which n is 0, it is desirable to increase the above-mentioned molar ratio. A greater molar ratio however results in more unreacted amine and thus, more time and labor are required for its removal after the reaction. Preferably, the molar ratio of the aromatic amine compound to the aralkyl alcohol is not greater than 10.

Illustrative examples of A in the aralkyl alcohol derivative, which is useful in the practice of suitable groups for use as substituent A in the alalkyl alcohol derivative represented by the formula (c), include

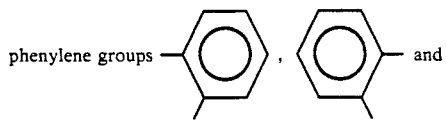

phenylene groups

alkyl-substituted phenylene groups

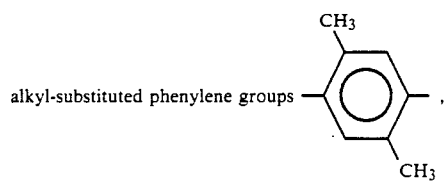

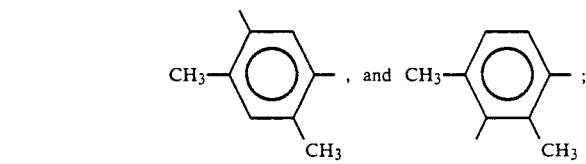

diphenylene group

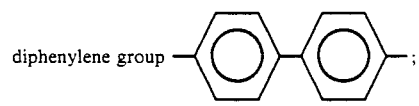

diphenyl ether group

naphthylenyl group

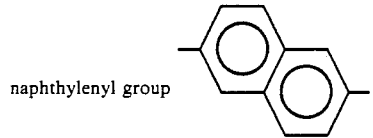

$R^2$ is a hydrogen atom or an acyl or alkyl group. When $R^2$ represents an acyl or alkyl group containing no more than four carbon atoms, the reaction velocity is high. When the carbon number is 4, and $R^2$ is a butyl group or tert-butyl group, the reaction proceeds at a low reaction velocity. Illustrative examples of aralkyl alcohol derivatives useful in the practice of this invention include α,α'-dihydroxy-o-xylene, α,α'-dihydroxy-m-xylene, α,α'-dihydroxy-p-xylene, α,α'-diacetoxy-o-xylene, α,α'-diacetoxy-m-xylene, α,α'-diacetoxy-p-xylene, α,α'-dipropionoxy-p-xylene, α,α'-di-n-butyloxy-p-xylene, α,α'-dimethoxy-o-xylene, α,α'-dimethoxy-m-xylene, α,α'-dimethoxy-p-xylene, α,α'-diethoxy-o-xylene, α,α'-diethoxy-m-xylene, α,α'-diethoxy-p-xylene, α,α'-diisopropoxy-o-xylene, α,α'-diisopropoxy-m-xylene, α,α'-diisopropoxy-p-xylene, α,α'-di-n-propoxy-p-xylene, α,α'-di-n-butoxy-m-xylene, α,α'-di-n-butoxy-p-xylene, α,α'-di-sec-butoxy-p-xylene, α,α'l-diisobutoxy-p- xylene, 4,4'-dihydroxymethyldiphenyl ether, 4,4'-dihydroxymethyldiphenyl, 2,6-dihydroxymethylnaphthalene, 4,4'-diacetoxymethyldiphenyl ether, 4,4'-diacetoxymethyldiphenyl, 2,6-diacetoxymethylnaphthalene, 4,4'-methoxymethyldiphenyl ether, 4,4'-methoxymethyldiphenyl, 4,4'-diethoxymethyldiphenyl ether, 4,4'-diisopropoxymethyldiphenyl, 4,4'-diisobutoxymethyldiphenyl ether, α,α'-dimethoxy-2-methyl-p-xylene, α,α'-dimethoxy-3-methyl-m-xylene, α,α'-dihydroxy-2,5-dimethyl-p-xylene, α,α'-dimethoxy-2,5-dimethyl-p-xylene, α,α'-dimethoxy-2,4-dimethyl-1,3-xylene, α,α'-dimethoxy-2,4-dimethyl-1,5-xylene, etc. Among these, α,α'-dimethoxy-p-xylene is preferred.

In the aromatic amine compound represented by the general formula (b), $R^1$ represents a halogen atom or a hydroxyl, $C_{1-4}$ alkoxy or $C_{1-5}$ alkyl group. The aromatic amine compound may contain 0–3 $R^1$ groups. When 2–3 $R^1$ groups are present, the groups may be either the same or different. Two of the $R^1$ groups may join together to form a 5-membered or 6-membered alicyclic group which may contain one or more side chains. The aromatic amine compound (b) may contain one or two amino groups. Exemplary aromatic amine compound, suitable for use in the process of the invention include aniline, o-toluidine, m-toluidine, o-ethylaniline, m-ethylaniline, p-ethylaniline, o-isopropylaniline, m-isopropylaniline, p-isopropylaniline, o-n-propylaniline, o-tert-butylaniline, p-tert-butylaniline, o-n-butylaniline, p-sec-butylaniline, 2,3-xylidine, 2,4-xylidine, 2,6-xylidine, 3,4-xylidine, 3,5-xylidine, 2-methyl-3-ethylaniline, 2-methyl-4-isopropylaniline, 2,6-diethylaniline, 2-ethyl-5-tert-butylaniline, 2,4-diisopropylaniline, 2,4,6-trimethylaniline, 4-chloroaniline, 4-bromoaniline, 4-fluoroaniline, 3-chloroaniline, 3-bromoaniline, 3,4-dichloroaniline, 3-chloro-o-toluidine, 3-chloro-p-toluidine, 2,6-dimethyl-4-chloroaniline, o-aminophenol, m-aminophenol, p-aminophenol, 2-amino-4-cresol, 4-amino-2-tert-butylphenol, 2,6-dimethyl-4aminophenol, 2,6-dichloro-4-aminophenol, 2-amino-1,3resorcin, 4-amino-1,3-resorcin, 2-aminohydroquinone, 2-methoxyaniline, 3-methoxyaniline, 4-methoxyaniline, 2-isopropoxyaniline, 2,4-dimethoxyaniline, o-phenylenediamine, m-phenylenediamine, p-phenylenediamine, 2,4-diaminotoluene, 2,6-diaminotoluene, 2,4-diaminoethylbenzene, 2,6-diaminoethylbenzene, 2,4-diaminoisopropylbenzene, 2,4-diamino-tert-butylbenzene, 2,6-diamino-tert-butylbenzene, 2,4-diamino-1,3dimethylbenzene, 1,1-dimethyl-4-aminoindane, 1,1-dimethyl-4,6-diaminoindane, etc. Preferably toluidines, xylidines, aminophenols and diamines, are employed. Most preferably, aniline is employed.

As the acid catalyst, it is preferred to use either singly or in combination an inorganic or organic acid, particularly a mineral acid, e.g., hydrochloric acid, phosphoric acid, sulfuric acid or nitric acid, a Friedel-Crafts catalyst such as zinc chloride, stannic chloride, aluminum chloride or ferric chloride, an organic sulfonic acid such as methanesulfonic acid or p-toluenesulfonic acid, or a super strong acid such as trifluoromethanesulfonic acid or "Nafion H" (trade name; product of E.I. du Pont de Nemours & Co., Inc.). Use of a solid acid catalyst such as an activated clay or zeolite, or a heteropolyacid is also suitable for use in the present process. In an industrial application hydrochloric acid is preferred due to its economical price. The acid catalyst may be used in an amount of from about 10 mole % or more, preferably from about 20–100 mole % based on the aromatic amine compound. Use of the catalyst in an amount less than 10 mole % results in a slow reaction velocity and thus makes it difficult to achieve complete conversion into primary amine compounds. Amounts greater than 100 mole % do not give adverse effects to the reaction but are not economical.

The reaction temperature is preferably 130° C. or higher. The reaction becomes extremely slow if the temperature is lower than 130.C. A temperature range of about 170°–240° C. is preferred in order to shorten the reaction temperature as much as possible. The reaction time may range from 10 hours to 40 hours. As a resin of the formula (a) having greater n groups is produced, the reaction time becomes shorter.

An inert solvent may be used in the reaction of the first production process according to this invention. However, the reaction is preferably carried out without a solvent. After completion of the reaction, the acid employed as a catalyst is neutralized, for example, with a dilute aqueous alkaline solution such as an aqueous solution of caustic soda, an aqueous solution of potassium hydroxide or aqueous ammonia and is then separated.

When unreacted aromatic amine compound remains in the above reaction, it is distilled out in vacuum or by steam distillation.

The second process of this invention for the production of the aromatic amine resin will next be described.

According to the second process of this invention, the aromatic amine compound represented by the general formula (b) and the bishalogenomethyl derivative represented by the general formula (d) can be reacted in two stages in the absence of a catalyst. In this case, a resin containing a secondary amine is formed in the first stage of the reaction. It is however only necessary to convert the secondary amine into a primary amine resin by a rearrangement reaction (second-stage reaction). In the rearrangement reaction hydrogen halide, which is produced upon formation of the primary amine resin, is used as a catalyst. However, in order to accelerate this rearrangement reaction, the reaction is conducted in the same manner as in the first production process of this invention, for example, (a) by increasing the amount of a catalyst of the same or different kind, (b) by increasing the reaction temperature or (c) by prolonging the reaction time, compared to the reaction conditions under which a secondary amine resin is formed. It is particularly effective to increase the amount of the catalyst.

Like the first production process, the second production process of this invention has also made it possible to freely produce aromatic amine resins, which range in properties from a low molecular resin composed principally of the aromatic amine compound of the general formula (a) in which n is 0, to a high molecular weight resin composed principally of the aromatic amine compound of the general formula (a) in which n is about 300. The resins obtaine by changing the molar ratio of the aromatic amine compound to the bishalogenomethyl derivative upon conducting the condensation reaction. Thus, it is possible to produce aromatic amine resins in various forms ranging from those in a liquid form at room temperature to those having a high softening point and resinous appearance in accordance with the intended end use. Specifically, aromatic amine resins ranging from liquid resins to low softening point resins can be obtained when the molar ratio of the aromatic amine compound to the bjshalogenomethyl derivative is increased in the condensation reaction. On the other hand, aromatic amine resins having a high softening point can be obtained when the molar ratio of the bishalogenomethyl derivative to the aromatic amine is about the stoichiometric ratio in the condensation reaction.

The molecular weight range and softening point range of the aromatic amine resins obtained in accordance with the second process of this invention are similar to those of the resins obtained in accordance with the first production process.

The aromatic amine compound represented by the general formula (b) is preferably added in an amount of from about 1-15 moles, preferably from about 1.1-10 moles per mole of the bishalogenomethyl derivative represented by the general formula (d). The compounds are heated. A suitable acid catalyst may be added in advance or in the course of the reaction in order to accelerate the reaction.

In the bishalogenomethyl derivative represented by the general formula (d), A is a phenylene group, an alkyl-substituted phenylene group, a diphenylene group, a diphenyl ether group, a naphthylenyl group or the like, and X is a chlorine, bromine, fluorine or iodine atom. Exemplary bishalogenomethyl derivatives useful in the practice of this invention include $\alpha,\alpha'$-dichloro-o-xylene, $\alpha,a'$-dichloro-m-xylene, $\alpha,\alpha'$l-dichloro-p-xylene, $\alpha,\alpha'$-dibromo-o-xylene, $\alpha,\alpha'$-dibromo-m-xylene, $\alpha,\alpha'$-dibromo-p-xylene, $\alpha,\alpha'$-difluoro-o-xylene, $\alpha,\alpha'$-difluoro-m-xylene, $\alpha,\alpha'$-difluoro-p-xylene, $\alpha,\alpha'$-diiodo-o-xylene, $\alpha,\alpha'$-diiodo-m-xylene, $\alpha,\alpha'$-diiodo-p-xylene, 4,4'-bis(chloromethyl)diphenyl ether, 4,4'-bis(chloromethyl)diphenyl, 2,6-bis(chloromethyl)naphthalene, 4,4'-bis(bromoethyl)diphenyl ether, 4,4'bis(bromomethyl)diphenyl, 2,6-bis(bromomethyl)naphthalene, 4,4'-bis(fluoromethyl)diphenyl ether, 4,4'-bis(fluoromethyl)diphenyl, 4,4'-bis(iodomethyl)diphenyl ether, 4,4'-bis(iodomethyl)diphenyl, $\alpha,\alpha'$-dichloro-2-methyl-p-xylene, $\alpha,\alpha'$-dichloro-3-methyl-m-xylene, $\alpha,\alpha'$-dichloro-2,5-dimethyl-p-xylene, $\alpha,\alpha'$-dibromo-2,5-dimethyl-p-xylene, $\alpha,\alpha'$-dichloro-2,4-dimethyl-1,3-xylene, $\alpha,\alpha'$-dichloro-2,4-dimethyl-1,5-xylene. Among these, $\alpha,\alpha'$-dichloro-p-xylene is preferred.

As $R^1$ in the aromatic amine compound of the general formula (b) employed in this invention, a similar atom or group as is in the first production process may be chosen as desired depending on the kind of the target aromatic amine. One or two amino groups are also contained therein. Its specific examples and the most preferable compound among such specific examples are hence as described above.

In the second production process of this invention, an acid catalyst may also be used to accelerate the reaction as mentioned above. As the acid catalyst, any one of acid catalysts usable in the first production process can be used. Industrially preferred is hydrochloric acid for its economical price. To the hydrogen halide which is formed in the course of the reaction, the catalyst may be added in an amount of from about 100 mole % or less based on the aromatic amine compound. Although no problems would arise even if the catalyst is added beyond that level, use of the catalyst in such an excess amount is not economical.

The reaction temperature may range from about 0° C. to about 240° C. during the reaction. However, it is preferred that the temperature be from about 0°-130° C., more preferably, 20°-100° C. in the first stage of the reaction and from about 130°-240° C. in the second-stage reaction. In order to shorten the reaction time of the second stage as much as possible, a temperature range of from about 170°-240° C. is desirable. The reaction time may be from about 1-10 hours in the first stage and from about 5-40 hours in the second stage. The reaction time also becomes shorter as a resin having greater n in the general formula (a) is produced.

An inert solvent may also be used in the reaction of the second production process according to this invention. However, the reaction is usually carried out without solvent. After completion of the reaction, the acid formed in the reaction or the acid employed as a catalyst is neutralized, for example, with a dilute aqueous alkaline solution such as an aqueous solution of caustic soda, an aqueous solution of potassium hydroxide or aqueous ammonia and is then separated.

When unreacted aromatic amine compound remains in the above reaction, it is distilled out in vacuum or by steam distillation.

The aromatic amine resin of this invention can be obtained in the above-described manner. Since the bishalogenomethyl derivative represented by the general formula (d) is used as a raw material, a catalyst is not absolutely required for the reaction, and thus aromatic amine resin can be produced at a more economical price, and the process produces fewer side reactions.

Thermosetting resin compositions according to this invention will next be described.

N,N'-4,4'-diphenylmethanebismaleimide represented by the formula (e) can be prepared with ease by subjecting 4,4'-diaminodiphenylmethane and maleic anhydride to a condensation/dehydration reaction by a method known per se in the art.

A thermosetting resin composition is then obtained from N,N'-4,4'-diphenylmethanebismaleimide represented by the formula (e) and the aromatic amine resin composed of a mixture of aromatic amine compounds represented by the formula (a). The following methods can be used to produce the thermosetting resin composition.

(1) The bismaleimide and aromatic amine resin can be ground and mixed in solid-solid forms or in solidliquid forms. As an alternative, the resins can be heat-treated into a prepolymer, followed by grinding into pellets or powder. It is preferable to choose such heating conditions that the resultant mixture is partially cured to the stage of the prepolymer. It is generally suitable to heat them at from about 70°-220° C. for from about 5-240 minutes, preferably at from about 80°-200° C. for from about 10-180 minutes.

(2) The bismaleimide and aromatic amine resin can be dissolved in an organic solvent. The resultant solution is charged into a bad solvent. Crystals thus precipitated are collected by filtration and then dried into pellets or powder. As an alternative, after dissolution in an organic solvent, the resins can be partially cured to the stage of a prepolymer by a heat treatment. The prepolymer is then charged into a bad solvent. Crystals thus precipitated are collected by filtration and then dried into pellets or powder. Conditions for the heat treatment should follow those employed in the method (1).

Suitable organic solvents for use in processes (1) and (2) above include halogenated hydrocarbons such as methylene chloride, dichloroethane and trichloroethylene, ketones such as acetone, methyl ethyl ketone, cyclohexanone and diisopropyl ketone, ethers such as tetrahydrofuran, dioxane and methylcellosolve, aromatic compounds such as benzene, toluene and chlorobenzene, and aprotic polar solvents such as acetonitrile, N,N-dimethylformamide, N,N-dimethylacetamide, dimethylsulfoxide, N-methyl-2-pyrrolidone and 1,3-dimethyl-2-imidazolidinone.

It is preferred that the aromatic amine resin composed of the mixture of the aromatic amine compounds represented by the formula (a) be used in an amount of from about 5–100 parts by weight, more preferably, from about 10–80 parts by weight per 100 parts by weight of N,N'-4,4'-diphenylmethanebismaleimide represented by the formula (e).

If the amount of the aromatic amine resin is smaller than 5 parts by weight, cured products obtained from the resultant composition may be extremely brittle and may not provide any satisfactory flexural strength. If the aromatic amine resin is used in an amount greater than 100 parts by weight the resultant cured products may have poor heat resistance.

The following components may be added to the thermosetting resin compositions of this invention as needed to such an extent that the objects of this invention are not impaired.

(a) Curing accelerators, for example, radical polymerization initiators such as azo compounds and organic peroxides, and ionic catalysts such as tertiary amines, quaternary ammonium salts, imidazoles, boron trifluoride and amine salts.

(b) Powdery reinforcing materials and fillers, for example, metal oxides such as aluminum oxide and magnesium oxide, metal hydroxides such as aluminum hydroxide, metal carbonates such as calcium carbonate and magnesium carbonate, diatomaceous earth, basic magnesium silicate, calcined clay, fine particulate silica, molten silica, crystalline silica, carbon black, kaolin, fine particulate mica, silica flour, graphite, asbestos, molybdenum disulfide, and antimony trioxide. In addition, fibrous reinforcing materials and fillers, for example, inorganic fibers such as glass fibers, rock wool, ceramic fibers, alumina fibers and potassium titanate fibers, and organic fibers such as carbon fibers and aromatic polyamide fibers may also be added.

(c) One or more synthetic resins may also be blended to improve the properties of the resin composition in end products such as coating films, bonding layers and resin moldings. Such synthetic resins may include thermosetting resins such as phenol resins, epoxy resins, melamine resins and silicone resins, polyamides, polycarbonates, polysulfones, polyether sulfones, polyether ether ketones, modified polyphenylene oxides, polyphenylene sulfides, polyether imides, and fluoroplastics.

The thermosetting resin compositions of this invention can be molded or otherwise formed for practical applications by known molding or forming methods such as compression molding, transfer molding, extrusion and injection molding.

This invention will hereinafter be described in more detail by the following Examples, which are intended to be purely exemplary of the invention. Example 1:

A reaction vessel fitted with a stirrer, a thermometer and a Dean-Stark's azeotropic distillation trap was charged with 111.6 g (1.2 moles) of aniline as an aromatic amine compound represented by the general formula (b), 66.5 g (0.4 mole) of $\alpha,\alpha'$-dimethoxy-p-xylene as an aralkyl alcohol derivative represented by the general formula (c) and 62.6 g (0.6 mole) of a 35% aqueous solution of hydrochloric acid as a catalyst. The contents were heated while feeding nitrogen gas. Water which began to be distilled out into the trap from an internal temperature of about 1100° C. was taken out of the system. When the internal temperature was raised further, distillation of methanol was observed from about 130° C. While distilling out methanol thus formed, the internal temperature was continuously raised. After reaching 170° C., the reaction mixture was maintained at the same temperature for 3 hours. Formation of methanol ceased substantially. The reaction mixture was thereafter heated further to 190°–200° C., at which the reaction was allowed to proceed for 12 hours. The reaction system was then cooled to lower the internal temperature to 95° C. To the thus-cooled reaction mixture, 168 g of a 15% aqueous solution of caustic soda was added and then stirred to neutralize the reaction mixture. After allowing the resultant mixture to stand, a water layer appeared as a lower layer was separated out. Saturated saline (300 g) was added to an upper layer to wash the same. The saline was then separated out. The resultant solution was heated and dried under a nitrogen gas stream and then filtered under pressure to remove inorganic salts and the like. The filtrate was concentrated in a vacuum of 2–3 mmHg to recover 51.9 g of unreacted aniline. The residue was taken out, thereby obtaining 94.5 g of an aromatic amine resin of a pale yellowish brown color.

The composition of the thus-obtained aromatic amine resin according to this invention was analyzed by high-performance liquid chromatography. As a result, it was found to have the following composition:

| Amine compound(s) of general formula (a) | n = 0 | n = 1 | n = 2 | n = 3 | n ≧ 4 |
|---|---|---|---|---|---|
| Mole % | 28 | 16.8 | 10.5 | 7.8 | 36.9 |

Further, the amine equivalent of the resin as measured by the perchloric acid-glacial acetic acid method was 0.578 equivalent/100 g. Its softening point as measured by a ring and ball softening point measuring instrument according to JIS (Japanese Industrial Standard) K-2548 was 68° C. In addition, its average molecular weight was 960.

Results of an IR analysis of the resin are sown in FIG. 1.

EXAMPLE 2

A reaction was conducted in the same manner as in Example 1 except for the use of 244.4 g (2.0 moles) of 2,4-diaminotoluene as an aromatic amine compound represented by the general formula (b) and 209 g (2.0 moles) of 35% hydrochloric acid as a catalyst, whereby 132 g of an aromatic amine resin was obtained as a reddish brown oil.

The composition of the thus-obtained aromatic amine resin according to this invention was analyzed by high-performance liquid chromatography. As a result, it was found to have the following composition:

| Amine compound(s) of general formula (a) | n = 0 | n = 1 | n = 2 | n ≧ 3 |
|---|---|---|---|---|
| Mole % | 44.5 | 29.7 | 14.6 | 11.2 |

The amine equivalent of the resin was 1.204. Its softening point and average molecular weight were 46° C. and 550 respectively.

EXAMPLE 3

A reaction was conducted in the same manner as in Example 1 except for the use of 121.1 g (1.3 moles) of aniline as an aromatic amine compound represented by the general formula (b), 138.28 g (1.0 mole) of α,α'-dihydroxy-m-xylene as an aralkyl alcohol derivative represented by the general formula (c) and 33 g (0.325 mole) of concentrated sulfuric acid as a catalyst, whereby 151 g of an aromatic amine resin of a pale yellowish brown color was obtained.

The amine equivalent of the thus-obtained aromatic amine resin was 0.496. Its softening point as measured by the ring and ball softening point measuring instrument according to JIS (Japanese Industrial Standard) K-2548 was 118° C. Its average molecular weight was 6500.

EXAMPLE 4

A reaction vessel was charged with 109 g (1.0 mole) of p-aminophenol as an aromatic amine compound represented by the general formula (b), 110.2 g (0.5 mole) of α,α'-diacetoxy-p-xylene as an aralkyl alcohol derivative represented by the general formula (c), and 6.8 g (0.05 mole) of zinc chloride and 19 g (0.1 mole) of p-toluene sulfonic acid as catalysts. They were reacted under reduced pressure by means of a water jet pump. The reaction started from about 130° C. and the internal temperature arose to 170° C. in 3 hours. Acetic acid generated in the course of the reaction was recovered in a deep-cooling trap. After maintaining the reaction mixture at the same temperature for 3 hours, the reaction temperature was raised further to 200° C., followed by aging at 200°-210° C. for 1 hour before completion of the reaction. The reaction mixture was cooled down to 95° C., at which 300 m of toluene was added to dissolve the reaction mixture under stirring. After adding 20.2 g of triethylamine to the resultant mixture, 200 ml of water was added. The thus-prepared mixture was stirred and then allowed to stand. A water layer that occurred as a lower layer was separated out. An upper layer was washed once again with 200 ml of water and the water was thereafter separated out. The resulting solution was concentrated in a vacuum to remove toluene and unreacted p-aminophenol. As a brown resin, 138 g of an aromatic amine resin was obtained.

The amine equivalent of the thus-obtained aromatic amine resin was 0.525. Its softening point as measured by the ring and ball softening point measuring instrument according to JIS (Japanese Industrial Standard) K-2548 was 94° C. Its average molecular weight was 2200.

EXAMPLE 5

A reaction was conducted in the same manner as in Example 1 except for the use of 745 (8.0 moles) of aniline, 664 g (4.0 moles) of α,α'-dimethoxy-p-xylene and 420 g (4.0 moles) of a 35% aqueous solution of hydrochloric acid as a catalyst, whereby 747 g of an aromatic amine resin of a pale yellowish brown color was obtained.

The composition of the thus-obtained aromatic amine resin according to this invention was analyzed by high-performance liquid chromatography. As a result, it was found to have the following composition:

| Amine compound(s) of general formula (a) | n = 0 | n = 1 | n = 2 | n ≧ 3 |
|---|---|---|---|---|
| Mole % | 17.0 | 14.5 | 13.2 | 55.2 |

The amine equivalent of the resin was 0.520 equivalent/100 g. Its softening point and average molecular weight were 61° C. and 2100 respectively.

EXAMPLES 6–14

Various aromatic amine resins of this invention as shown in Table 1 were obtained by separately conducting reactions in the same manner as in Example 1 except that the kind of the aromatic amine compound represented by the general formula (b), the kind and amount of the aralkyl alcohol derivative represented by the general formula (c) and the kind and amount of the catalyst and the reaction conditions were selected as shown in Table 1.

TABLE 1
Syntheses of Various Aromatic Amine Resins

| Ex. | Aromatic amine Kind | Amount (mole) | Aralkyl alcohol derivatives Kind | Amount (mole) | Catalyst Kind | Amount (mole) | Reaction conditions Temp./time (°C.) (hr) | Synthesized resin Structural unit | Yield (g) | M.W. | S.P.* (°C.) |
|---|---|---|---|---|---|---|---|---|---|---|---|
| 6 | o-Toluidine | 1.2 | 4,4'-Dihydroxy-methyldiphenyl ether | 0.12 | HCl | 0.4 | 140–170/5 170–195/12 | $\left[\begin{array}{c}\text{NH}_2\text{-C}_6\text{H}_3(\text{CH}_3)\text{-CH}_2\text{-C}_6\text{H}_4\text{-O-C}_6\text{H}_4\text{-CH}_2\end{array}\right]_n$ | 50.5 | 580 | Oily |
| 7 | 2,4-Xylidine | 1.2 | α,α'-Diisopropoxy-p-xylene | 0.4 | " | 0.6 | 130–170/5 170–200/8 | $\left[\begin{array}{c}\text{NH}_2\text{-C}_6\text{H}_2(\text{CH}_3)_2\text{-CH}_2\text{-C}_6\text{H}_4\text{-CH}_2\end{array}\right]_n$ | 116 | 1350 | 75 |
| 8 | 2,4,6-Trimethyl-aniline | 1.2 | α,α'-Dihydroxy-2,5-dimethyl-p-xylene | 0.3 | " | 0.24 | 130–170/5 200–210/8 | $\left[\begin{array}{c}\text{NH}_2\text{-C}_6\text{H}(\text{CH}_3)_3\text{-CH}_2\text{-C}_6\text{H}_2(\text{CH}_3)_2\text{-CH}_2\end{array}\right]_n$ | 92 | 850 | 70 |
| 9 | p-n-Propyl-aniline | 1.2 | α,α'-Dimethoxy-p-xylene | 1.0 | " | 0.6 | 130–150/5 180–200/14 | $\left[\begin{array}{c}\text{NH}_2\text{-C}_6\text{H}_3(\text{n-C}_3\text{H}_7)\text{-CH}_2\text{-C}_6\text{H}_4\text{-CH}_2\end{array}\right]_n$ | 246 | 12000 | 142 |

TABLE 1-continued

Syntheses of Various Aromatic Amine Resins

| Ex. | Aromatic amine Kind | Amount (mole) | Aralkyl alcohol derivatives Kind | Amount (mole) | Catalyst Kind | Amount (mole) | Reaction conditions Temp./time (°C.) (hr) | Synthesized resin Structural unit | Yield (g) | M.W. | S.P.* (°C.) |
|---|---|---|---|---|---|---|---|---|---|---|---|
| 10 | m-Isopropoxy-aniline | 1.2 | α,α'-Dimethoxy-p-xylene | 0.4 | " | 0.24 | 130–150/3 170–190/6 | 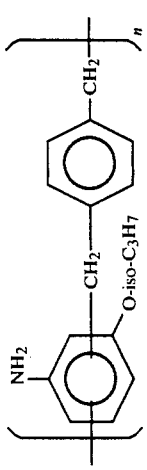 | 120 | 1200 | 56 |
| 11 | p-Chloro-aniline | 1.2 | α,α'-Dimethoxy-p-xylene | 0.4 | H$_3$PO$_4$ | 0.24 | 150–170/3 190–200/8 | 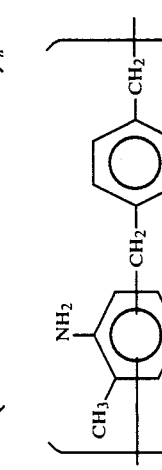 | 118 | 1150 | 78 |
| 12 | 4-Chloro-o-toluidine | 1.2 | α,α'-Dimethoxy-p-xylene | 0.4 | HCl | 0.6 | 150–170/5 190–200/12 | 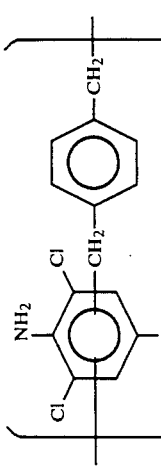 | 120 | 1100 | 75 |
| 13 | 3,5-Dichloro-4-aminophenol | 1.2 | α,α'-Dimethoxy-p-xylene | 0.4 | " | 0.6 | 150–170/5 170–190/12 | 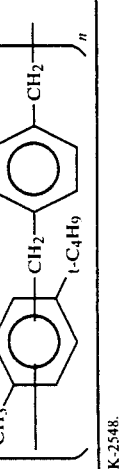 | 135 | 1250 | 75 |
| 14 | 5-tert-Butyl-o-toluidine | 1.2 | α,α'-Dimethoxy-p-xylene | 0.4 | CF$_3$SO$_3$H | 0.15 | 130–150/3 170–190/6 |  | 142 | 1520 | 87 |

*Softening point as measured by the ring and ball softening point measuring apparatus according to JIS (Japanese Industrial Standard) K-2548.

EXAMPLE 15

In 1400 g of dry o-dichlorobenzene, 100 g of the aromatic amine resin obtained in Example 1 was dissolved. Thereafter, 253 g of phosgene was blown at 5°–10° C. into the solution over 3 hours. While slowly blowing phosgene into the solution, the solution was heated and aged at 120°–140° C. for 2 hours. The feeding of phosgene was then stopped and switched over to the feeding of nitrogen gas. The reaction system was thoroughly purged with nitrogen gas and was then cooled. The reaction mixture was concentrated in a vacuum to recover o-dichlorobenzene as the solvent, so that 111 g of an isocyanated resin were obtained in the form of a pale brown oil.

In 400 g of methylene chloride, 10.4 g of the isocyanated resin obtained as described above was dissolved to provide "Solution A". "Solution B", which consisted of 2.2 g of "EDTDA" (product of Ethyl Corporation), 10 g of "JEFFAMINE T-5000" (trade name; product of Texaco Chemical Company) and 2500 g of methylene chloride, was then mixed with the abovementioned "Solution A". The resultant mixture was cast on a glass plate. It was allowed to stand overnight, followed by post curing at 120° C. for 2 hours. A good polyurea film was successfully obtained.

EXAMPLE 16

Forty (40) parts by weight of the aromatic amine obtained in Example 1 were mixed with 100 parts by weight of "Bismaleimide-s" (trade name; product of Daiwa Kasei Co., Ltd.). The resultant mixture was heated and cured at 180° C. for 10 minutes to prepare a prepolymer.

The solubility of the prepolymer in various solvents was measured. Results are summarized under Experiment 1 in Table 2. In addition, the external appearance, softening point, gelling time and bulk specific gravity of the prepolymer are summarized under Experiment 1 in Table 3. For the sake of comparison, commercial "Kerimid-1050" (trade name; molding grade; product of Nippon Polyimide Co., Ltd.) was also tested similarly. Results are shown under Comparative Experiment 1 in Table 2 and Table 3 respectively.

Next, the prepolymer and "Kerimid-1050" were separately subjected to compression molding at 200° C. under 40 kg/cm² for 1 hour. The resultant moldings were thereafter post-cured at 250° C. for 4 hours, thereby producing test pieces of cured resins. Mechanical strengths and thermal properties of the test pieces were measured. Results are shown respectively under Experiment 1 and Comparative Experiment 1 in Table 3.

TABLE 2

| | Solubility of Heat-Cured Prepolymer (wt. %) Measured at 25° C. | |
|---|---|---|
| Solvent | Experiment 1 Aromatic amine resin/bismaleimide-s | Comparative Experiment 1 Kerimid-1050 |
| N-Methylpyrrolidone | >50 | >50 |
| N,N-Dimethylacetamide | >50 | >50 |
| N,N-Dimethylformamide | >50 | 48 |
| 1,4-Dioxane | 35 | <1 |
| Diethylene glycol dimethyl ether | <1 | <1 |
| m-Cresol | 38 | 34 |
| Methylene chloride | 28 | <1 |
| Trichloroethylene | <1 | <1 |
| Benzene | <1 | <1 |
| Toluene | <1 | <1 |
| Methoxybenzene | <1 | <1 |
| Acetone | <1 | <1 |
| Methyl ethyl ketone | <1 | <1 |

TABLE 3

| | Basic Physical Properties | | | |
|---|---|---|---|---|
| Tested property | Testing method | Unit | Experiment 1 Aromatic amine resin/bismaleimide-s | Comparative Experiment 1 Kerimid-1050 |
| Prepolymer | | | | |
| External appearance | — | — | Yellow powder | Yellow powder |
| Softening point | Capillary method | °C. | 105 | 107 |
| Gelling time | 200° C. hot plate method | sec | 62–73 | 56–68 |
| Bulk specific gravity | JIS K-6911 | g/cc | 0.44 | 0.42 |
| Molding post-cured at 250° C. for 4 hours) | | | | |
| Specific gravity | JIS K-6911 | — | 1.30 | 1.31 |
| Flexural strength | JIS K-6711, 25° C. | kg/mm² | 12.8 | 8.6 |
| Flexural modulus | JIS K-6911, 25° C. | kg/mm² | 372 | 352 |
| Izod impact strength | JIS K-6911, un-notched | kg · cm/cm | 18 | 13 |
| Barcol hardness | ASTM D 2583 | — | 45 | 47 |
| Heat distortion temp. | JIS K-6911, 18.5/cm² | °C. | >260 | >260 |
| Pyrolysis starting temperature | TGA method, heating rate: 10° C./min | °C. | 341 | 322 |
| Glass transition temperature | TMA penetration method | °C. | >300 | >300 |
| Expansion coefficient | JIS K-6911 | cm/cm/°C. | $5.69 \times 10^{-5}$ | $5.89 \times 10^{-5}$ |
| Water absorption rate | 25° C./24 hrs, immersed in water | % | 0.48 | 0.91 |

EXAMPLE 17

A reaction vessel fitted with a stirrer and a thermometer was charged with 111.6 g (1.2 moles) of aniline as an aromatic amine compound represented by the general formula (b) and 70.0 g (0.4 mole) of α,α'-dichloro-p-xylene as a bishalogenomethyl derivative represented by the general formula (d). The contents were heated while feeding nitrogen gas. Although evolution of heat was observed from an internal temperature of about 30° C., the contents were continuously heated and maintained at 85°–100° C. for 3 hours (first-stage reaction). They were thereafter heated and reacted at 190°–200° C. for 20 hours (second-stage reaction). The reaction system was then cooled to lower the internal temperature to 95° C. To the thus-cooled reaction mixture, 230 g of a 15% aqueous solution of caustic soda was added. They were stirred to neutralize the reaction mixture. After allowing the resultant mixture to stand, a water layer appeared as a lower layer was separated out. Saturated saline (300 g) was added to an upper layer so as to wash the same. The resultant solution was heated and dried under a nitrogen gas stream and was then filtered under pressure to remove inorganic salts and the like. The filtrate was concentrated in a vacuum of 2–3 mmHg to recover 48.5 g of unreacted aniline. The residue was taken out, thereby obtaining 100 g of an aromatic amine resin of a pale yellowish brown color.

The composition of the aromatic amine resin obtained by the second process of this invention as described above was analyzed by high-performance liquid chromatography. As a result, it was found to have the following composition:

| Amine compound(s) of general formula (a) | $n = 0$ | $n = 1$ | $n = 2$ | $n = 3$ | $n \geq 4$ |
|---|---|---|---|---|---|
| Mole % | 27.8 | 19.2 | 14.0 | 11.8 | 27.2 |

Further, the amine equivalent of the resin as measured by the perchloric acid-glacial acetic acid method was 0.65 equivalent/100 g. Its softening point as measured by a ring and ball softening point measuring instrument according to JIS (Japanese Industrial Standard) K-2548 was 64° C. In addition, its average molecular weight was 880.

EXAMPLE 18

The procedure of Example 17 was repeated except that 61.1 g (0.5 mole) of 2,4-diaminotoluene and 29.2 g (0.1 mole) of α,α'-dibromo-2,5-dimethyl-p-xylene were used as an aromatic amine compound represented by the general formula (b) and a bishalogenomethyl derivative represented by the general formula (d) respectively and the reaction time of the second stage was changed to 30 hours, whereby 32.5 g of an aromatic amine resin was obtained.

The composition of the aromatic amine resin thus obtained by the second process of this invention as described above was analyzed by high-performance liquid chromatography. As a result, it was found to have the following composition:

| Amine compound(s) of general formula (a) | $n = 0$ | $n = 1$ | $n = 2$ | $n \geq 3$ |
|---|---|---|---|---|
| Mole % | 41.8 | 21.2 | 13.1 | 23.9 |

The amine equivalent of the resin was 1.212. Its softening point and average molecular weight were 46° C. and 520 respectively.

EXAMPLE 19

The procedure of Example 17 was repeated except for the use of 53.6 g (0.5 mole) of mixed toluidine, which consisted of 19% of the o-isomer, 53% of the m-isomer and 28% of the p-isomer, and 106.9 g (0.4 mole) of 4,4'-bis(chloromethyl)diphenyl ether as an aromatic amine compound represented by the general formula (b) and a bishalogenomethyl derivative represented by the general formula (d) respectively, whereby 116 g of an aromatic amine resin was obtained.

The amine equivalent of the aromatic amine resin obtained by the second process of this invention as described above was 0.35. Its softening point as measured by the ring and ball softening point measuring instrument according to JIS (Japanese Industrial Standard) K-2548 was 136° C. Its average molecular weight was 13200.

EXAMPLE 20

A reaction vessel similar to that employed in Example 17 was charged with 93.1 g (1 mole) of aniline as an aromatic amine compound represented by the general formula (b) and 17.5 g (0.1 mole) of a,al-dichloro-m-xylene as a bishalogenomethyl derivative represented by the general formula (d). The contents were heated while feeding nitrogen gas. Although evolution of heat was observed from an internal temperature of about 30° C., the contents were continuously heated and maintained at 70°–80° C. for 5 hours (first-stage reaction). Next, 31.3 g (0.3 mole) of a 35% aqueous solution of hydrochloric acid was charged into the reaction mixture, and the resultant mixture was heated as was. Water formed in the course of the heating was distilled out of the system. They were thereafter reacted at 180°–190° C. for 16 hours (second-stage reaction). Cooling, stirring and neutralization, separation and removal, washing and separation, heating and drying, pressure filtration and vacuum concentration were then carried out as in Example 17, thereby obtaining 25 g of an aromatic amine resin as a pale brown oil.

The composition of the aromatic amine resin obtained by the second process of this invention as described above was analyzed by high-performance liquid chromatography. As a result, it was found to have the following composition:

| Amine compound(s) of general formula (a) | $n = 0$ | $n = 1$ | $n = 2$ | $n = 3$ |
|---|---|---|---|---|
| Mole % | 79.0 | 17.7 | 2.7 | 0.6 |

Further, the amine equivalent of the resin was 0.674, and its average molecular weight was 330.

EXAMPLE 21

The procedure of Example 20 was repeated except for the use of 17.5 g (0.1 mole) of α,α'-dichloro-p-xylene as a bishalogenomethyl derivative represented by the general formula (d) and the use of 19.0 g (0.1 mole) of p-toluenesulfonic acid as a reaction accelerator before the second-stage reaction, thereby obtaining 25.8 g of an aromatic amine resin as a pale brown oil.

The amine equivalent of the aromatic amine resin obtained by the second process of this invention adescribed above was 0.671. Its composition was substantially the same as the resin obtained in Example 20.

EXAMPLES 22–25

A stainless reaction vessel fitted with a stirrer, a reflux condenser and a nitrogen inlet tube was charged with N,N'-4,4'-diphenylmethanebismaleimide and the aromatic amine resin, which was obtained in Example 1, in amounts given respectively in terms of parts by weight in Table 4. The contents were heated and cured at 180° C. for 20 minutes, followed by defoaming ing at 150° C. under reduced pressure (10-15 mmHg) for 30 minutes. The melt was then cooled down to room temperature. In the above-described manner, resin compositions were separately obtained in a form solidified in a brown transparent glassy state.

While separately heating and melting the compositions, they were individually filled in molds heated at 180° C. and were then maintained under 50 kg/cm² at 200° C. for 30 minutes to perform compression molding. Resultant moldings were taken out of the respectivl molds and then post-cured for 4 hours in an oven of 250° C., thereby obtaining test pieces of cured resins whose length, width and thickness were 127 mm, 12.7 mm and 6.4 mm respectively.

The heat distortion temperatures of those test pieces were measured in accordance with ASTM D-648 while their bending tests were conducted in accordance with ASTM D-790. In addition, their pyrolysis starting temperatures were also measured at a heating rate of 10.C/min in air. Results are summarized in Table 4.

EXAMPLES 26-38 & COMPARATIVE EXAMPLES 1-2

The procedure of Examples 22-25 was repeated using 100 parts by weight of N,N'-4,4'-diphenylmethanebismaleimide and the aromatic amine resins, which are given in Table 4, in amounts indicated in terms of parts by weight in Table 4. Results are also shown in Table 4.

COMPARATIVE EXAMPLE 3

The procedure of Examples 22-25 was repeated except for the use of N,N'-4,4'-diphenylmethanebismaleimide and 4,4'-diaminodiphenylmethane in their respective amounts shown in terms of parts by weight in Table 4. Results are also given in Table 4.

COMPARATIVE EXAMPLE 4

Moldings were produced in the same manner as in Examples 22-25 by using "Kerimid-1050" (trade name for a polyaminobismaleimide resin; product of Japan Polyimide Co., Ltd.) instead of the resin compositions of this invention. various physical properties were measured. Results are also given in Table 4.

The results set forth in Table 4 show that the thermosetting resin compositions of this invention are high in both flexural strength and flexural modulus and also have excellent heat resistance as demonstrated by the heat distortion temperatures all above 290° C. and pyrolysis temperatures all above 340° C.

TABLE 4

Examples 22-38 & Comparative Examples 1-4

| | Bismaleimide (wt. parts) | | Aromatic amine resin (wt. parts) | Flexural strength (kg/mm²) | Flexural modulus (kg/mm²) | Heat distortion (°C.) | Pyrolysis starting temp. (°C.) |
|---|---|---|---|---|---|---|---|
| Ex. 22 | N,N'-4,4'-Diphenyl-methanebismaleimide | (100) | Ex. 1 (10) | 10.2 | 351 | >300 | 371 |
| Ex. 23 | N,N'-4,4'-Diphenyl-methanebismaleimide | (100) | Ex. 1 (30) | 12.0 | 365 | >300 | 369 |
| Ex. 24 | N,N'-4,4'-Diphenyl-methanebismaleimide | (100) | Ex. 1 (50) | 12.8 | 372 | >300 | 362 |
| Ex. 25 | N,N'-4,4'-Diphenyl-methanebismaleimide | (100) | Ex. 1 (80) | 11.5 | 370 | 297 | 357 |
| Ex. 26 | N,N'-4,4'-Diphenyl-methanebismaleimide | (100) | Ex. 5 (50) | 11.9 | 389 | >300 | 360 |
| Ex. 27 | N,N'-4,4'-Diphenyl-methanebismaleimide | (100) | Ex. 2 (50) | 11.9 | 375 | 294 | 354 |
| Ex. 28 | N,N'-4,4'-Diphenyl-methanebismaleimide | (100) | Ex. 3 (50) | 12.6 | 370 | >300 | 361 |
| Ex. 29 | N,N'-4,4'-Diphenyl-methanebismaleimide | (100) | Ex. 4 (50) | 11.3 | 369 | >300 | 356 |
| Ex. 30 | N,N'-4,4'-Diphenyl-methanebismaleimide | (100) | Ex. 6 (50) | 13.1 | 389 | 290 | 350 |
| Ex. 31 | N,N'-4,4'-Diphenyl-methanebismaleimide | (100) | Ex. 7 (50) | 11.7 | 387 | 294 | 342 |
| Ex. 32 | N,N'-4,4'-Diphenyl-methanebismaleimide | (100) | Ex. 8 (10) | 12.0 | 375 | 297 | 349 |
| Ex. 33 | N,N'-4,4'-Diphenyl-methanebismaleimide | (100) | Ex. 9 (50) | 12.0 | 380 | >300 | 351 |
| Ex. 34 | N,N'-4,4'-Diphenyl-methanebismaleimide | (100) | Ex. 10 (50) | 12.4 | 370 | >300 | 350 |
| Ex. 35 | N,N'-4,4'-Diphenyl-methanebismaleimide | (100) | Ex. 11 (50) | 11.9 | 383 | >300 | 351 |
| Ex. 36 | N,N'-4,4'-Diphenyl-methanebismaleimide | (100) | Ex. 12 (50) | 11.7 | 383 | >300 | 352 |
| Ex. 37 | N,N'-4,4'-Diphenyl- | (100) | Ex. 13 (50) | 12.0 | 371 | >300 | 353 |

TABLE 4-continued

Examples 22-38 & Comparative Examples 1-4

| | Bismaleimide (wt. parts) | | Aromatic amine resin (wt. parts) | Flexural strength (kg/mm²) | Flexural modulus (kg/mm²) | Heat distortion (°C.) | Pyrolysis starting temp. (°C.) |
|---|---|---|---|---|---|---|---|
| Ex. 38 | N,N'-4,4'-Diphenyl-methanebismaleimide | (100) | Ex. 14 (50) | 12.2 | 376 | >300 | 341 |
| Comp. Ex. 1 | N,N'-4,4'-Diphenyl-methanebismaleimide | (100) | — (0) | Molding was infeasible. (Cracks were formed.) | | | 418 |
| Comp. Ex. 2 | N,N'-4,4'-Diphenyl-methanebismaleimide | (100) | Ex. 1 (150) | 8.9 | 349 | 280 | 331 |
| Comp. Ex. 3 | N,N'-4,4'-Diphenyl-methanebismaleimide | (100) | 4,4'-diamino-diphenylmethane (30) | 8.6 | 352 | 276 | 330 |
| Comp. Ex. 4 | Kerimid-1050 | | | 8.6 | 352 | 285 | 333 |

As has been described above, the aromatic amine resins of this invention are composed of primary amines and hence facilitate isocyanation, maleimidation and epoxidation. Accordingly, they are also useful as raw materials for polyamides and the like.

When the aromatic amine resins of this invention are used as curing agents or raw materials for other resins, the resulting resins have excellent mechanical strength, dimensional stability, heat resistance, and stability to light and oxygen in air, and their curing speeds are also high.

The aromatic amine resins of this invention can readily provide prepolymers because they are soluble in a solvent of a low melting point.

Since the aromatic amine resins of this invention have such advantageous effects, they can be used in a wide variety of fields, for example, as curing agents, raw materials for cured resins, chelate resins, ion-exchange resins, molding materials, insulating paints, bonding agents, rubber modifiers, additives to various resins, deacidification agents, and raw materials for polyimides, polyamides and polyamideimides, etc.

Further, the aromatic amine resins of this invention can be produced from economical raw materials by a simple operation, and can be obtained by a process which is practically free of pollution and byproducts. It is also possible to produce aromatic amine resins in various forms, ranging from those in a liquid form at room temperature to those in a resinous form having a high softening point, in accordance with the end use. In the second production process of this invention in particular, there are such merits that catalyst is not absolutely required for the reaction, the aromatic amine resins can be produced economically, and less side reactions take place.

In addition, the thermosetting resins according to this invention have superb mechanical strength and heat resistance. They are hence expected to find wide-spread utility in fields in which high heat resistance is required in recent years, for example, the electrical and electronic field, the mechanical field such as aircrafts and vehicles, and the like field. They can therefore be used advantageously in the industry.

Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

We claim:

1. A thermosetting resin composition comprising about 100 parts by weight of N,N'-4,4'-diphenylmethanebismaleimide represented by formula (e):

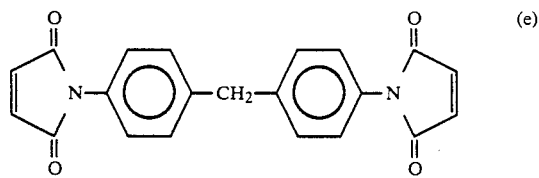

and from about 5 to about 100 parts by weight of an aromatic amine resin comprising a mixture of aromatic amine compounds represented by the formula (a):

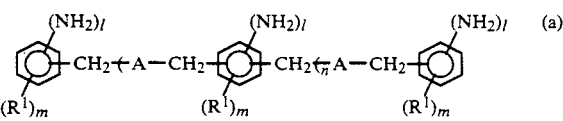

wherein A represented a phenylene, alkyl-substituted phenylene, diphenylene, diphenyl ether or napthylenyl group, $R^1$ represents a halogen atom, a hydroxyl group, a $C_1$–$C_4$ alkoxy or a $C_1$–$C_5$ lkyl group, l is 1 or 2, m is 0, 1, 2 or 3, n is an integer from 0 to 300 and when m is 2 or 3 and said $R^1$ groups are thes ame or different and two $R^1$ groups may join to form a 5- or 6-membered alicyclic moiety.

2. The thermosetting resin composition of claim 1, wherein l is 1 and m is 0.

3. The thermosetting resin composition of claim 2, wherein n is 0, 1, 2, 3 or 4.

4. The thermosetting resin composition of claim 3, where A is a phenylene group.

5. The thermosetting resin composition of claim 1, wherein A is a phenylene group.

6. The thermosetting resin composition of claim 5, wherein l is 1 and m is 0.

7. The thermosetting resin composition of claim 1, wherein m is 2 or 3 and two said $R^1$ groups join to form a 5- or 6-membered alicyclic moiety having at least one side chain.

* * * * *

UNITED STATES PATENT AND TRADEMARK OFFICE
CERTIFICATE OF CORRECTION

PATENT NO. : 5,051,494

DATED : September 24, 1991

INVENTOR(S) : YAMAGUCHI ET AL.

It is certified that error appears in the above-identified patent and that said Letters Patent is hereby corrected as shown below:

In column 26, formula (a), after "$CH_2$" (third occurrence, amend "(" to --)--;

In column 26, line 46, amend "represented" to --represents--;

In column 26, line 51, amend "thes ame" to --the same--; and

In column 26, lines 49, 55 and 63, amend "1" to ----.

Signed and Sealed this

Eighteenth Day of May, 1993

Attest:

MICHAEL K. KIRK

*Attesting Officer*   *Acting Commissioner of Patents and Trademarks*